United States Patent [19]

Trybulski et al.

[11] Patent Number: 4,990,520

[45] Date of Patent: Feb. 5, 1991

[54] 2-,4- OR 5-SUBSTITUTED THIAZOLE DERIVATIVES

[75] Inventors: Eugene J. Trybulski, Park Ridge, N.J.; Herbert J. Brabander, Nanuet, N.Y.

[73] Assignee: American Cyanamid Company, Wayne, N.J.

[21] Appl. No.: 474,573

[22] Filed: Feb. 2, 1990

[51] Int. Cl.$^5$ ................. A61K 31/425; A61K 31/445; C07D 417/06; C07D 277/28

[52] U.S. Cl. .................................... 514/326; 514/365; 546/209; 548/202

[58] Field of Search ................... 546/209; 548/202; 514/326, 365

[56] References Cited

U.S. PATENT DOCUMENTS 4,788,207 11/1988 Lutomski et al. .................. 548/202

Primary Examiner—Robert T. Bond
Attorney, Agent, or Firm—Kenneth J. Dow

[57] ABSTRACT

Pharmaceutical compounds and compositions which may be represented by the following structural formulae:

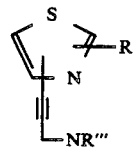

where R is hydrogen or lower alkyl and NR''' is amino, ($C_1$-$C_6$) alkylamino, dialkylamino, or trialkylamino, pyrrolidino or piperidino. The compounds are useful in treating central cholinergic disfunction in mammals.

21 Claims, No Drawings

2-,4- OR 5-SUBSTITUTED THIAZOLE DERIVATIVES

CROSS REFERENCE TO RELATED APPLICATION

The subject matter of this application is related to that of applicant's co-pending application Ser. No. 07/382,813 filed July 19, 1989.

BACKGROUND OF THE INVENTION

The present invention relates to novel 2-,4-or 5-substituted thiazole compounds, pharmaceutical compositions containing the compounds and to the use of the compounds for the treatment of central cholinergic disfunction.

The novel compounds described herein are useful as cholinergic agents. A chronic deficiency in central cholinergic function has been implicated in a variety of neurologic and psychiatric disorders, including Senile Dementia of the Alzheimer's type (SDAT), tardive dyskinesia, Pick's disease and Huntington's chorea. Post mortem neurochemical investigations of patients with SDAT have demonstrated a reduction in presynaptic markers for acetylcholine-utilizing neurons in the hippocampus and the cerebral cortex. [P. Davies and A. J. R. Maloney, Lancet, 1976-II, 1403, (1976); E. K. Perry, R. H. Perry , G. Blessed, B. E. Tomlinson, J. Neurol. Sci., 34, 247, (1976)]. The basis for this cholinergic abnormality is unclear, but evidence suggests that the cholinergic neurons in the neuclues basalis of Meynert may selectively degenerate in SDAT [J. T. Coyle, D. J. Price, M. R. DeLong, Science, 219, 1184, (1983)]. If this degeneration plays a role in behavior symptoms of the disease, then a possible treatment strategy would be to compensate for the loss of cholinergic output to the cortex and hippocampus.

In an aged monkey animal model, designed to mimic the symptoms of SDAT, the direct muscarinic agonists arecoline [R. T. Bartus, R. L. Dean, B. Beer, Neurobiology of Aging, 1, 145, (1980)]and oxotremorine [R. T. Bartus, R. L. Dean, B. Beer, Psyohopharmacology Bulletin, 19, 168, (1983)]produced significant improvement in performance. These results in aged monkeys were corroborated in SDAT patients with arecoline which produced a more-consistent improvement when compared to the anticholinesterase inhibitor physostigmine [J. E. Christie, A. Shering, J. Ferguson, A. M. Glen, British Journal of Psychiatry, 138, 46, (1981)].

These animal behavioral and clinical results have instigated significant efforts in a search for a muscarinic agonist which will selectively compensate for the loss of cholinergic input in the hippocampus and cereberal cortex. However, the search must be refined to seek agonists Which will not effect significantly the remaining body cholinergic functions. The recent disclosure (T. I. Bonner, N. J. Buckley, A. C. Young, M. R. Brann, Science, 237,527, (1987)] that muscarinic receptors are not all the same but exist as a heterogenous population of receptors substantiates the possibility for the discovery of a selective muscarinic agonist.

N-methyl-N-(1-methyl-4-pyrrolidino-2-butynyl) acetamide(BM-5) having the structure set forth below, has been reported to be a presynaptic cholinergic antagonist (which should disinhibit the release of endogenous acetylcholine) and a postsynaptic partial cholinergic agonist (which should mimic the effects of acetylcholine). See Resul. B. and co-workers, Eur. J. Med. Chem., 1982, 17. 317.

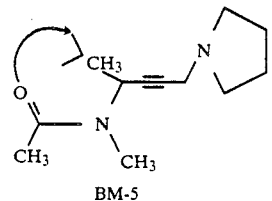

BM-5 (a)

Chemically, BM-5 is a fairly flexible molecule that can assume a number of different conformations. The present invention describes the synthesis of a series of novel (3-amino-1-propynyl)thiazoles which are derivatives of BM-5 in which one degree of freedom (bond a) has been restricted.

SUMMARY OF THE INVENTION

This invention is concerned with new compounds described by the following Formula I:

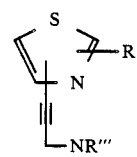

I where R is selected from hydrogen or lower alkyl, NR''' is selected from NR'' and NR'; NR'' is $(C_1-C_6)$-trialkylamino; NR' is amino, $(C_1-C_6)$alkylamino, $(C_1-C_6)$ dialkylamino, pyrrolidino or piperidino; and pharmaceutically acceptable acid addition salts thereof. The compounds have cholinergic activity and accordingly, the invention includes methods for treating diseases of the central nervous system in mammals employing these new compounds; with pharmaceutical preparations containing these compounds; and with processes for the production of these compounds.

DESCRIPTION OF THE INVENTION

The novel compounds of the present invention may be prepared in accordance with the following Scheme I, wherein —NR' is selected from amino, $(C_1-C_6)$alkylamino, $(C_1-C_6)$dialkylamino, pyrrolidino or piperidino; NR'' is trialkylamino; and $R^{iv}$ X is a $(C_1-C_6)$alkyl halide.

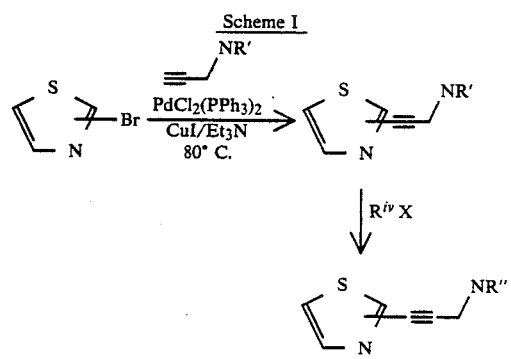

The synthesis of the 2-, 4- or 5-substituted thiazoles is accomplished by palladium (o) catalyzed coupling reactions between the appropriate propargylamine and a 2-, 4- or 5-bromothiazole in the presence of a base such as a tertiary amine and a cuprous halide at the reflux temperature for several hours, giving the desired product. Reaction of the amine product NR' with a $(C_1-C_6)$alkyl halide gives the quaternary ammonium salt where NR'' is $(C_1-C_6)$trialkylamino.

Whereas the 4- and 5-(3-amino-1-propynyl)-thiazoles formed hydrochloride salts in the expected manner, the treatment of 2-(3-amino-1-propynyl) thiazoles with methanolic hydrogen halide (X=Cl, Br,I) gives the hydrohalide addition products across the triple bond as shown in Scheme II.

Scheme II

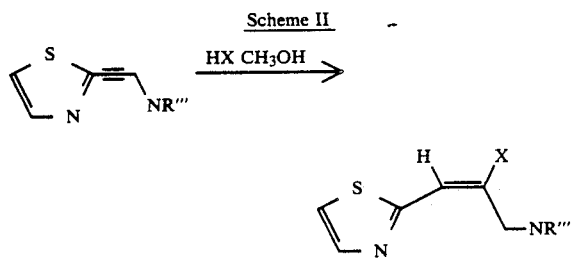

The compounds of this invention were tested for cholinergic activity according to the following procedures.

[$^3$H] Quinuclinyl Benzilate Binding Assay

This assay is utilized in conjunction with the $^3$H-Cis-methyldioxolane binding assay to evaluate antagonist and high affinity agonist binding properties of CNS cholinergic agents. The procedure is adapted from Watson, M., Yamamura, H. I., and Roeske, W. R., J. Pharmacol. Exp. Ther. 237: 411–418 (1986) and Watson, M., Roeske, W. R., and Yamamura, H. I., J. Pharmacol. Exp. Ther. 237: 419–427 (1986).

Tissue Preparation:

Rats are sacrificed by decapitation and the brain removed and placed on ice. The cerebral cortex is dissected on a cold stage, weighed and homogenized (Polytron, setting 5.5 with PT-10 saw-tooth generator for 15 seconds) in 50 volumes (wet wt/vol) of ice-cold 10 mM (8.1 mM $Na_2HPO_4$, 1.9 mM $KH_2PO_4$) sodium-potassium phosphate buffer (NaKPB), pH 7.4. The homogenate is placed in an ice bath for 30 seconds and homogenized again as above. This procedure is repeated once again for a total of three times. The resulting homogenate is then diluted 1:3000 (original wet wt/vol) With ice-cold NaKPB for use in the assay. The final protein content per 2.0 ml of incubation mixture is 0.1 mg.

Dilution of Compounds:

A stock solution of Atropine is prepared at 0.2 mM to define non-specific binding (1 μM final conc). Test compounds are prepared at 40 mM (final conc 1 mM) in buffer (if water soluble) or in absolute ethanol - 1 N HCl (1:1, v/v) and serially diluted to the desired concentrations. In general, dose-response profiles are examined between 1 mM and 1 pM final concentrations.

Preparation of $^3$H-QNB:

$^3$H-QNB (NEN, NET-656; specific activity=30.0 Ci/mmol) is diluted to 5 nM, with NaPB (final concentration =0.25 nM activity −18,000 cpm at a counting efficiency of 55%).

$^3$H-QNB Binding Assay:

A typical protocol is outlined below:

| Tube No. | ID* | Buffer μL | Atropine μL | Test Compound μL | $^3$H-QNB μL | Tissue ml |
|---|---|---|---|---|---|---|
| 1–2 | Total | 50 | — | — | 100 | 1.85 |
| 3–4 | NS | 40 | 10 | — | " | " |
| 5–6 | 4e-11 | — | — | 50 | " | " |
| 7–8 | 4e-10 | — | — | " | " | " |
| 9–10 | 4e-09 | — | — | " | " | " |
| 11–12 | 4e-08 | — | — | " | " | " |
| 13–14 | 4e-07 | — | — | " | " | " |
| 15–16 | 4e-06 | — | — | " | " | " |
| 17–18 | 4e-05 | — | — | " | " | " |
| 19–20 | 4e-04 | — | — | " | " | " |
| 21–22 | 4e-03 | — | — | " | " | " |
| 23–24 | 4e-02 | — | — | " | " | " |

*Stock concentration [M] of compound to be tested.

Components are added in the following order: test compound, pound, radioligand, buffer or tissue to give a final volume of 2.0 ml. After adding the tissue homogenate, the tubes are thoroughly mixed and incubated at 25° C. for 120 minutes. At the end of 120 minutes, the samples are filtered through GF/B glass fiber filters (Whatman) using a 24 sample cell harvester (Brandel) under a vacuum of 15 mm Hg. The tubes are washed with 5×3 ml ice-cold NaKPB. The filters are then placed in scintillation vials with 10 ml of scintillation cocktail (Beckman HP or HP/B), allowed to stand overnight, shaken and then counted. Specific binding is calculated as Total—NS (non-specific). The percent is inhibition of specific binding is then calculated and the IC50 values computed using either the LIGAND or LUNDON software packages for competition binding. The results of this test on representative compounds of this invention appear in Table I.

[$^3$H]-Cis-methyldioxolane Binding Assay (High Affinity)

This assay is utilized in conjunction with $^3$H-QNB binding to evaluate high affinity agonist binding and and tagonist properties of CNS cholinergic agents. The procedure is adapted from Vickroy, T. W., Roeske, W. R, and Yamamura, H. I., J. Pharmacol. Exp. Ther. 229: 747–755 (i984). This is a rapid filtration assay that is set up to label only the high affinity agonist conformation of the muscarinic cholinergic receptor.

Tissue Preparation:

Rats are sacrificed by decapitation and the brain removed and placed on ice. The cerebral cortex is dissected on a cold stage, weighed and homogenized (Polytron, setting 5.5 with Pt-10 saw-tooth generator for 15 seconds in 50 volumes (wet wt/vol) of ice-cold 10 mM (8.1 mM $Na_2HPO_4$, 1.9 mM $KH_2PO_4$) sodium-potassium phosphate buffer (NaKPB), pH 7.4. The homogenate is placed in an ice bath for 30 seconds and homogenized again as above. This procedure is repeated once again for a total of three times. The resulting homogenate is then diluted 1:300 (original wet wt/vol) with ice-cold NaKPB for use in the assay. The final protein content per 2.0 ml of incubation mixture is 0.75 mg.

Dilution of Compounds:

A stock solution of Atropine is prepared at 0.2 mM to define non-specific binding 1 μM final conc). Test compounds are prepared at 40 mM (final conc 1 mM) in buffer (if water soluble) or in absolute ethanol-1 N HCl (1:1, v/v) and serially diluted to the desired concentrations. In general, dose-response profiles are examined between 1 mM and 1 pM final concentrations.

Preparation of $^3$H-CD:

$^3$H-CD (NEN, NET-647; specific activity=55.5 Ci/mmol) is diluted to 20 nM with NaPB (final conc=1.0 nM, activity −75,000 cpm at a counting efficiency of 55%).

Technical Notes:

$^3$H-CD adheres readily to both glass and plastic surfaces. To eliminate this problem (and the chance for introducing artifacts into the results), stock vials, pipette tips and all glass tubes are routinely treated with Prosil-28, a siliconizing agent, and oven dried prior to use in an assay. Additionally, the GF/B glass fiber filters are pre-soaked in an aqueous polyethylenimine (PEI) solution (0.1%, pH 7.0) prior to use.

All points in the inhibition curve (including total and non-specific binding) are always measured on single PEI treated filter strips to minimize filter-to-filter variability. (see Bruns, R. F., et al. Anal. Biochem. 132: 74–81 (1983) for the use of PEI treated filters in filtration receptor assays).

The $^3$H-CD is prepared fresh in buffer just prior to use in the assay to avoid possible decomposition. It should be kept on an ice bath after dilution in buffer.

$^3$H-CD Binding Assay:

A typical protocol is outlined below:

| Tube No. | ID* | Buffer μL | Atropine μL | Test Compound μL | $^3$H-CD μL | Tissue ml |
|---|---|---|---|---|---|---|
| 1-2 | Total | 50 | — | — | 100 | 1.85 |
| 3-4 | NS | 40 | 10 | — | " | " |
| 5-6 | 4e-11 | — | — | 50 | " | " |
| 7-8 | 4e-10 | — | — | " | " | " |
| 9-10 | 4e-09 | — | — | " | " | " |
| 11-12 | 4e-08 | — | — | " | " | " |
| 13-14 | 4e-07 | — | — | " | " | " |
| 15-16 | 4e-06 | — | — | " | " | " |
| 17-18 | 4e-05 | — | — | " | " | " |
| 19-20 | 4e-04 | — | — | " | " | " |
| 21-22 | 4e-03 | — | — | " | " | " |
| 23-24 | 4e-02 | — | — | " | " | " |

*Stock concentration [M] of compound to be tested.

Components are added in the following order: compound, radioligand, buffer or tissue to give a final volume of 2.0 ml. After adding the tissue homogenate, the tubes are thoroughly mixed and incubated at 25° C. for 120 minutes. At the end of 120 minutes, the samples are filtered through PEI pretreated GF/B glass fiber filters (Whatman) using a 24 sample cell harvester (Brandel) under a vacuum of 15 mm Hg. The tubes are washed with 5×3 ml ice-cold NaKPB. The filters are then placed in scintillation vials with 10 ml of scintillation cocktail (Beckman HP or HP/B), allowed to stand overnight, shaken and then counted. Specific binding is calculated is Total—NS (non-specific). The percent inhibition of specific binding is then calculated and the IC50 values computed using either the LIGAND or LUNDON software packages for competition binding. The results of this test on representative compounds of this invention appear in Table I.

TABLE I

| Compound | $^3$H-QNB IC$_{50}$ μM | $^3$H-CD IC$_{50}$ nM |
|---|---|---|
| 2-[3-(1-Pyrrolidinyl)-1-propynyl]thiazole | 44 | 1426 |
| 1-[3-(2-Thiazolyl)-2-propynyl]piperidine | 182 | 10180 |
| N,N-Dimethyl-3-(2-thiazolyl)-2-propyn-1-amine | 1311 | 9978 |
| N,N,N-Trimethyl-3-(2-thiazolyl)-2-propyn-1-aminium, iodide | 123 | 673 |
| 2-[2-Chloro-3-(1-pyrrolidinyl)-1-propenyl]thiazole | 186 | 2230 |
| 1-[2-Chloro-3-(2-thazolyl)-2-propenyl]piperidine | 117 | 6594 |
| 2-Chloro-N,N-dimethyl-3-(2-thiazolyl)-2-propen-1-amine | 222 | 1069 |
| 2-[2-Bromo-3-(1-pyrrolidinyl)-1-propenyl]thiazole | 90 | |
| 4-[3-(1-Pyrrolidinyl)-1-propynyl]thiazole | 71 | 3954 |
| 1-[3-(4-Thiazolyl)-2-propynyl]piperidine | 124 | 28140 |
| 1-[3-(4-Thiazolyl)-2-propynyl]piperidine, hydrochloride | 114 | 14010 |
| N,N-Dimethyl-3-(4-thiazolyl)-2-propyn-1-amine | 504 | 12920 |
| N,N-Dimethyl-3-(4-thiazoyl)-2-propyn-1-amine | 381 | 19030 |
| N,N,N-Trimethyl-3-(4-thiazolyl)-2-propyn-1-aminium, iodide | 119 | 1459 |
| 5-[3-(1-Pyrrolidinyl)-1-propynyl]thiazole | 73 | 245 |
| 1-[3-(5-Thiazolyl)-2-propenyl]piperidine | 164 | 12640 |
| N,N-Dimethyl-3-(5-thiazolyl)-2-propyn-1-amine | 765 | 3375 |
| N,N,N-Trimethyl-3-(5-thiazolyl)-2-propyn-1-amine, iodide | 131 | 273 |
| 5-[3-(1-Pyrrolidinyl)-1-propynyl]thiazole | 115 | 4699 |
| 1-[3-(5-Thiazolyl)-2-propynyl]piperidine, monohydrochloride | 119 | 658 |
| N,N-Dimethyl-3-(5-thiazolyl)-2-propyn-1-amine, monohydrochloride | 482 | |

Those compounds which have $^3$H-CD IC$_{50}$ values of <1000 nM and/or $^3$H-QNB IC$_{50}$ values of <1000 μM are considered active.

The effective dosage of active ingredient employed may vary with the particular compound employed, the mode of administration, and the severity of the condition being treated. In general, however, satisfactory results are obtained when the compounds of the invention are administered at a daily dosage of from about 0.02 mg to about 100 mg/kg of patient body weight, preferably given in divided doses two to four times a day, or in sustained release form. For most patients, the total daily dosage is from about 1 mg to about 5,000 mg, preferably from about 1 mg to 20 mg.

The pharmaceutical preparations of the present invention may contain, for example, from about 0.5% up to about 90% of the active ingredient in combination with the carrier, more usually between 5% and 60% by weight. This dosage regimen may be adjusted to provide the optimal therapeutic response. For example, several divided doses may be administered daily or the dose may be proportionally reduced as indicated by the exigencies of the therapeutic situation.

Dosage forms suitable for internal use comprise from about 0.25 to 5.0 mg of the active compound in intimate admixture with a solid or liquid pharmaceutically acceptable carrier. A decided practical advantage is that these active compounds may be administered orally as well as by intravenous, intramuscular, or subcutaneous routes if necessary. Solid carriers include starch, lactose, dicalcium phosphate, microcrystalline cellulose, sucrose, and kaolin, while liquid carriers include sterile Water, polyethylene glycols, non-ionic surfactants, and edible oils such as corn, peanut, and sesame oils, as are appropriate to the nature of the active ingredient and the particular form of administration desired. Adjuvants customarily employed in the preparation of pharmaceutical compositions may be advantageously included, such as flavoring agents, coloring agents, and antioxidants, e.g., vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exits. It must be stable under the conditions or manufacture and storage and must be preserved against the contaminating action of microorganisms such as bacteria and fungi. The carrier can be a solvent or dispersion medium containing, for example, water ethanol, polyol (e.g., glycerol, propylene glycol, and liquid polyethylene glycol), suitable mixtures thereof, and vegetable oils.

As used herein, "pharmaceutically acceptable carriers" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in therapeutic compositions is contemplated.

The following examples describe in detail the chemical synthesis of representative compounds of the present invention. The procedures are illustrations, and the invention should not be construed as being limited by chemical reactions and conditions they express. No attempt has been made to optimize the yields obtained in these reactions, and it would be obvious to one skilled in the art that variations in reaction times, temperatures, solvents, and/or reagents could increase the yields.

The following Reference Examples describe the preparation of the intermediates used to make some of the final products in this invention.

Reference Example 1

2,4-Dibromothiazole

Following the procedure of P. Reynaud, et al., Bul. Soc. Chim. France, 1735-8, 1962; a mixture of 6.3 g of 2,4-thiazolidine-dione and 50 g of phosphorus oxybromide is stirred at 110°-115° C. for 3 hours. The reaction is poured into 250 g of ice treated portionwise with 80 ml of 10 N sodium hydroxide and 250 ml of methylene chloride. The solution is filtered through diatomaceous earth, the layers are separated and the aqueous layer is re-extracted with methylene chloride. Sodium chloride is added to the aqueous phase and re-extracted with diethyl ether. The organic layers are combined, dried over sodium sulfate, filtered and concentrated in vacuo to give 10.7 g of product. The dibromide is purified by chromatography to give 7.6 g of the product as white crystals, m.p. 70°-72° C.

Reference Example 2

4-Bromothiazole

Following the procedure of M. Robba and R. C. Moreau, Annales pharm. franc. 22, #3, 201-210 (1965); 10 g of 2,4-dibromothiazole and 5 g of powdered zinc in 40 ml of glacial acetic acid is stirred at 60°-65° C. for 45 minutes. The mixture is cooled in an ice bath, as 40 ml of 10 N sodium hydroxide is added in portions. Stirring is continued for 30 minutes. Ten milliliters of 10 N sodium hydroxide is added and the reaction is extracted with diethyl ether followed by methylene chloride. The combined organic layers are dried over sodium sulfate, filtered and concentrated in vacuo to give 5.4 g of the product as a yellow oil. The $^1$H PMR spectrum indicates the presence of thiazole (10%) as an impurity. Chromatography is used to remove any additional impurities after the final coupling reactions.

Reference Example 3

5-Bromothiezole

The procedure of H. C. Beyerman, et al., Rev. Trav. Chim. 73,325 (1954) is used for the preparation of this intermediate. To a stirred mixture of 27.2 g of 2-amino-5-bromothiazole in 212 ml of 86% phosphoric acid is added at room temperature 43 ml of concentrated nitric acid. The mixture is cooled to −10° C. and a solution of 15.9 g of sodium nitrite in 52 ml of water is added slowly over 45 minutes, while maintaining the temperature between −5° to −10° C. The reaction is stirred at the low temperature for an additional 30 minutes. Eighty milliliters of 50% hypophosphorous acid is added over 75 minutes, maintaining the temperature between −5° C. and −10° C., followed by stirring for 2 hours at −5° C. The reaction mixture is stirred at room temperature for 16 hours and carefully added to a cooled solution of 161.5 g of sodium hydroxide in water. Ice is added to keep the reaction temperature under control. The reaction is extracted with methylene chloride, passed through a pad of diatomaceous earth and concentrated in vacuo to give 13.4 g of a dark brown oil. The crude 5-bromothiazole is purified by Kugelrohr distillation to give 10.2 g of colorless oil, b.p. 70°-80° C. (20 mm Hg).

Reference Example 4

1-(2Propynyl)piperidine, hydrochloride

Following the procedure of J. J. Biel and F. DiPierro, JACS, 80, 4609 (1958), 87.6 g of propargyl bromide (80% by wt. in toluene) is added over 40 minutes with stirring to an ice cooled solution of 102.2 g of piperidine in 600 ml of dry diethyl ether. The reaction mixture is stirred under mild reflux of 6 hours followed by stirring at room temperature for 16 hours. The precipitate is filtered, washed 3 times with ether and the combined filtrates are concentrated in vacuo at 50° under water aspirator pressure. The 1-(2-propynyl)-piperidine is purified by distillation is give 52.5 g of pure product, b.p. 55°–60° C. (5 mm Hg). The hydrochloride salt of the product is prepared by the addition of an excess ethanolic hydrogen chloride to a solution of the amine in ether. The hydrochloride salt of the product is recrystallized from acetonitrile to give the product as a crystalline solid, m.p. 180°–182° C.

The following Examples pertain to the preparation of final products encompassed by the present invention.

Example 1

N,N-Dimethyl-3-(2-thiazolyl)-2-propyn-1-amine

A mixture of 5.02 g of 2-bromothiazole, 20 ml of triethylamine, and 4.3 ml of 1-dimethylamino-2-propyne is stirred under argon for 5 minutes. Seven hundred and fifty milligrams of bis(triphenylphosphine) palladium (II) chloride and 0.450 mg of copper (I) iodide is added and the stirred reaction is heated at 80°–85° C. for 3 hours. The reaction mixture is cooled, partitioned between diethyl ether and 65 ml of 10% sodium carbonate, and the layers are separated. The organic layer is filtered through diatomaceous earth, washed with aqueous sodium chloride and dried over magnesium sulfate. The crude product is purified by chromatography using silica gel as absorbant followed by filtration of the product band through a pad of magnesium silicate to give 0.35 g of the desired product as an oil, MH+ 167. Purity is determined by $^1$H PMR spectroscopy and by thin layer chromatography.

Table II sets forth compounds which may be prepared by the procedure of Example 1 using appropriately substituted starting materials.

TABLE II

| Example # | Product | mp °C. or mass spectrum m/e (MH+) |
|---|---|---|
| 2 | N,N-Dimethyl-3-(4-thiazolyl)-2-propyn-1-amine | oil(MH+)=167 |
| 3 | N,N-Dimethyl-3-(4-thiazolyl)-2-propyn-1-amine, hydrochloride | mp 145–147° C. |
| 4 | N,N-Dimethyl-3-(5-thiazolyl)-2-propyn-1-amine | oil(MH+)=167 |
| 5 | N,N-Dimethyl-3-(5-thiazolyl)-2-propyn-1-amine, hydrochloride | mp 145–147° C. |
| 6 | 2-[3-(1-Pyrrolidinyl)-1-propynyl]thiazole | oil(MH+)=193 |
| 7 | 4-[3-(1-Pyrrolidinyl)-1-propynyl]thiazole | oil(MH+)=193 |
| 8 | 4-[3-(1-Pyrrolidinyl)-1-propynyl]thiazole, hydrochloride | mp 190–192° C. |
| 9 | 5-[3-(1-Pyrrolidinyl)-1-propynyl]thiazole | oil(MH+)=193 |
| 10 | 5-[3-(1-Pyrrolidinyl)-1-propynyl]thiazole, hydrochloride | mp 206–208° C. |
| 11 | 1-[3-(2-Thiazolyl)-2-propynyl]piperidine | oil(MH+)=193 |
| 12 | 1-[3-(4-Thiazolyl)-2-propynyl]piperidine | oil(MH+)=207 |
| 13 | 1-[3-(4-Thiazolyl)-2-propynyl]piperidine, hydrochloride | mp 219–221° C. |
| 14 | 1-[3-(5-Thiazolyl)-2-propynyl]piperidine | oil(MH+)=207 |
| 15 | 1-[3-(5-Thiazolyl)-2-propynyl]piperidine, hydrochloride | mp 210–212° C. |

Example 16

N,N,N-Trimethyl-3-(2-thiazolyl)-2-propyn-1-aminium iodide

A mixture of 0.7 g of N,N-dimethyl-3-(2-thiazolo)-2-propyn-1-amine prepared by the procedure of Example I and 2 ml of methyl iodide in 5 ml of diethyl ether is stirred at room temperature for 2 hours. The precipitate is collected by filtration to give 1.2 g of the crude product. Recrystallization of the product from acetonitrile gives colorless crystal, mp 217°–219° C.

Table III sets forth compounds which may be prepared by the procedure of Example 16 using appropriately substituted starting materials.

TABLE III

| Example # | Product | mp °C. or mass spectrum m/e (MH+) |
|---|---|---|
| 17 | N,N,M-Trimethyl-3-(4-thiazolyl)-2-propyn-1-aminium iodide | mp 220–222° C. |
| 18 | N,N,N-Trimethyl-3-(5-thiazolyl)-2-propyn-1-aminium iodide | mp 195–197° C. |

Hydrohalide addition across the triple bond

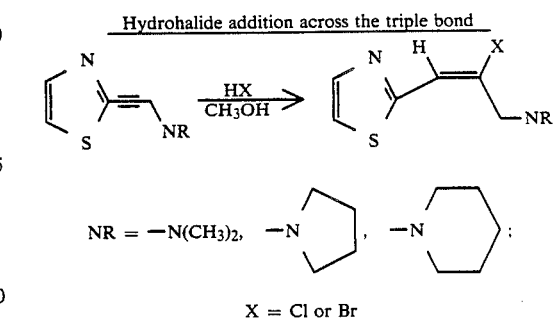

X = Cl or Br

Whereas the 4- and 5-(3-amino-1-propynyl)thiazoles formed hydrohalides in a normal manner, the addition of methanolic hydrogen chloride or methanolic hydrogen bromide to the 2-(3-amino-1-propynyl)thiazoles yielded the 2-halo-2-propen-1-amines listed below in Table IV. The position of the halogen is determined by $^1$HPMR spectral analysis.

TABLE IV

| Example # | Product | mp °C. or mass spectrum m/e (MH+) |
|---|---|---|
| 19 | 2-Chloro-N,N-dimethyl-3-(2-thiazolyl)-2-propen-1-amine,(E) | oil(MH+) = 203 |
| 20 | 1-[2-Bromo-3-(2-thiazolyl)-2-propenyl]piperidine,(E) | oil(MH+) = 288 |
| 21 | 2-[2-Chloro-3-(1-pyrrolidinyl)-1-propenyl]thiazole,(E) | oil(MH+) = 229 |
| 22 | 1-[2-Chloro-3-(2-thiazolyl)-2-propenyl]piperidine,(E) | oil(MH+) = 243 |
| 23 | 2-[2-Bromo-3-(1-pyrrolidinyl)-1-propenyl]thiazole,(E) | waxy solid MH+ = 274 |

We claim:

1. A compound selected from those of the Formulae:

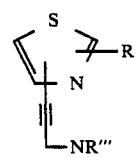

wherein R is selected from hydrogen or (C$_1$–C$_6$) alkyl; NR‴ is selected from NR″ and NR′ where NR′ is selected from amino, (C$_1$–C$_6$)alkylamino, (C$_1$–C$_6$)dialkylamino, pyrrolidinyl, piperidinyl and NR″ is (C$_1$–C$_6$)- trialkylamino; and the pharmaceutically acceptable acid addition salts thereof "and wherein NR" is $(C_1-C_6)$ trialkylamino the accompanying anion is a halide".

2. A compound according to claim 1 wherein R is hydrogen or $(C_1-C_6)$ and NR' is amino.

3. A compound according to claim 1 wherein R is hydrogen or $(C_1-C_6)$alkyl and NR' is $(C_1-C_6)$alkylamino.

4. A compound according to claim 1 wherein R is hydrogen or $(C_1-C_6)$alkyl and NR" is $(C_1-C_6)$dialkylamino.

5. A compound according to claim 1 wherein R is hydrogen or $(C_1-C_6)$alkyl and NR" is $(C_1-C_6$ trialkylamino.

6. A compound according to claim 1 wherein R is hydrogen or $(C_1-C_6)$alkyl and NR' is pyrrolidinyl.

7. A compound according to claim 1 wherein R is hydrogen or $(C_1-C_6)$alkyl and NR' is piperidinyl.

8. The compound according to claim 1, N,N,N-trimethyl-3-(2-thiazolyl)-2-propyn-1-aminium, iodide.

9. The compound according to claim 1, N,N-dimethyl-3-(4-thiazolyl)-2-propyn-1-amine.

10. The compound according to claim 1, N,N,N-trimethyl-3-(4-thiazolyl)-2-propyn-1-aminium, iodide.

11. The compound according to claim 1, N,N-dimethyl-3-(5-thiazolyl)-2-propyn-1-amine.

12. The compound according to claim 1, N,N,N-trimethyl-3-(5-thiazolyl)-2-propyn-1-aminium, iodide.

13. The compound according to claim 1, 2-[3-(1-pyrrolidinyl)-1-propynyl]thiazole.

14. The compound according to claim 1, 4-[3-(i-pyrrolidinyl)-1-propynyl]thiazole.

15. The compound according to claim 1, 5-[3-(1-pyrrolidinyl)-1-propynyl]thiazole.

16. The compound according to claim 1, 1-[3-(2-thiazolyl)-2-propynyl]piperidine.

17. The compound according to claim 1, 1-[3-(4-thiazolyl)-2-propynyl]piperidine.

18. The compound according to claim 1, 1-[3-(5-thiazolyl)-2-propynyl]piperidine.

19. The compound according to claim 1, N,N-Dimethyl-3-(2-thiazolyl)-2-propyn-1-amine.

20. A method of treating central cholinergic disfunction in a mammal which comprises administering to said animal an effective amount of the compound selected from those of claim 1.

21. A pharmaceutical composition of matter in dosage unit form comprising from about 1 mg to about 500 mg of a compound selected from those of claim 1 in association with a pharmaceutically acceptable carrier.

* * * * *